United States Patent
Kim et al.

(10) Patent No.: US 11,028,420 B2
(45) Date of Patent: Jun. 8, 2021

(54) METHOD FOR PRODUCING D-PSICOSE FROM D-PSICOSE BORATE COMPLEX USING CHROMATOGRAPHY AND COMPOSITION CONTAINING D-PSICOSE

(71) Applicant: CJ CHEILJEDANG CORPORATION, Seoul (KR)

(72) Inventors: Min Hoe Kim, Incheon (KR); Joo Hang Lee, Ansan-Si (KR); Hye Jin Jo, Suwon-Si (KR); Seong Bo Kim, Seongnam-Si (KR); Yang Hee Kim, Suwon-Si (KR); Jung Eun Kim, Suwon-Si (KR); Seung Won Park, Yongin-Si (KR); Eun Jung Choi, Seongnam-Si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/624,973

(22) PCT Filed: Jun. 22, 2018

(86) PCT No.: PCT/KR2018/007100
§ 371 (c)(1),
(2) Date: Dec. 20, 2019

(87) PCT Pub. No.: WO2018/236184
PCT Pub. Date: Dec. 27, 2018

(65) Prior Publication Data
US 2020/0172945 A1 Jun. 4, 2020

(30) Foreign Application Priority Data
Jun. 23, 2017 (KR) .................. 10-2017-0079637

(51) Int. Cl.
*C12P 19/02* (2006.01)
*B01D 15/18* (2006.01)
*B01D 15/36* (2006.01)
*C07H 1/06* (2006.01)
*C07H 3/02* (2006.01)
*C12P 19/24* (2006.01)

(52) U.S. Cl.
CPC ............ *C12P 19/02* (2013.01); *B01D 15/185* (2013.01); *B01D 15/362* (2013.01); *C07H 1/06* (2013.01); *C07H 3/02* (2013.01); *C12P 19/24* (2013.01)

(58) Field of Classification Search
None
See application file for complete search history.

(56) References Cited

U.S. PATENT DOCUMENTS

| 4,133,696 | A | 1/1979 | Barker et al. |
| 8,735,106 | B2 | 5/2014 | Hong et al. |
| 9,938,515 | B2 | 4/2018 | Cho et al. |
| 2012/0244580 | A1 | 9/2012 | Hung et al. |
| 2015/0210996 | A1 | 7/2015 | Woodyer et al. |
| 2016/0152967 | A1 | 6/2016 | Cho et al. |

FOREIGN PATENT DOCUMENTS

| KR | 10-2011-0035805 A | 4/2011 |
| KR | 10-1030192 B1 | 4/2011 |
| KR | 10-1384992 B1 | 4/2014 |
| KR | 10-1455759 B1 | 10/2014 |
| KR | 10-2016-0062349 A | 6/2016 |

OTHER PUBLICATIONS

International Search Report from International Application No. PCT/KR2018/007100, dated Feb. 5, 2019.
Written Opinion from International Application No. PCT/KR2018/007100, dated Feb. 5, 2019.
Hicks, Kevin B. et al., "Removal of Boric Acid and Related Compounds from Solutions of Carbohydrates with a Boron-selective Resin (IRA-743)", Carbohydrate Research, 1986, vol. 147, No. 1, pp. 39-48
Kim, Nam-Hee et al., "Conversion Shift of D-Fructose to D-Psicose for Enzyme-Catalyzed Epimerization by Addition of Borate", Applied and Environmental Microbiology, 2008, vol. 74, No. 10, pp. 3008-3013.
Lim, Byung-Chul et al., "A stable immobilized D-psicose 3-epimerase for the production of D-psicose in the presence of borate", Process Biochemistry, 2009, vol. 44, No. 8, pp. 822-828.
Nguyen, Van Duc Long et al., "Separation of D-psicose and D-fructose using simulated moving bed chromatography", Journal of Separation Science, 2009, vol. 32, No. 11, pp. 1987-1995.
Xu, Yonglan et al., "Technologies for Boron Removal", Industrial & Engineering Chemistry Research, 2008, vol. 47, No. 1, pp. 16-24
Extended European Search Report issued in corresponding European Patent Application No. EP 18820578, dated Mar. 10, 2021, 8 pages.

*Primary Examiner* — Layla D Berry
(74) *Attorney, Agent, or Firm* — Merchant & Gould P.C.

(57) ABSTRACT

The present application relates to a method for producing D-psicose, the method comprising the steps of: putting a composition containing a D-psicose borate complex into a chromatography comprising divalent cations; and separating the composition containing the D-psicose borate complex into a D-psicose-containing fraction (i) and a borate-containing fraction (ii).

13 Claims, 3 Drawing Sheets
Specification includes a Sequence Listing.

```
                          SEQUENCE LISTING

<160> NUMBER OF SEQ ID NOS: 4

<210> SEQ ID NO 1
<211> LENGTH: 289
<212> TYPE: PRT
<213> ORGANISM: Artificial Sequence
<220> FEATURE:
<223> OTHER INFORMATION: Amino acid sequences of the triple-mutant from
      D-psicose 3-epimerase

<400> SEQUENCE: 1

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Leu Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Pro Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 2
<211> LENGTH: 289
<212> TYPE: PRT
```

<213> ORGANISM: Artificial Sequence
<220> FEATURE:
<223> OTHER INFORMATION: Amino acid sequences of the double-mutant from
      D-psicose 3-epimerase

<400> SEQUENCE: 2

```
Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Leu Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Tyr Ala Arg
        115                 120                 125

Gly Val Glu Gly Ile Asn Gly Ile Ala Asp Phe Ala Asn Asp Leu Gly
130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly
```

<210> SEQ ID NO 3
<211> LENGTH: 289
<212> TYPE: PRT
<213> ORGANISM: Artificial Sequence
<220> FEATURE:
<223> OTHER INFORMATION: Amino acid sequences of D-psicose 3-epimerase

<400> SEQUENCE: 3

```
Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30
```

Ile Glu Val Ala Ala His His Ile Asn Glu Tyr Ser Asp Ala Glu Leu
           35                  40                  45

Ala Thr Ile Arg Lys Ser Ala Lys Asp Asn Gly Ile Ile Leu Thr Ala
 50                  55                  60

Gly Ile Gly Pro Ser Lys Thr Lys Asn Leu Ser Ser Glu Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
        210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly

<210> SEQ ID NO 4
<211> LENGTH: 297
<212> TYPE: PRT
<213> ORGANISM: Artificial Sequence
<220> FEATURE:
<223> OTHER INFORMATION: Amino acid sequence of D-psicose 3-epimerase
      from Kaistia granuli

<400> SEQUENCE: 4

Met Lys Asn Lys Leu Gly Val His Ala Gln Val Trp Val Gly Gly Trp
 1               5                  10                  15

Ser His Ala Glu Ala Glu Arg Ala Ile Ala Ser Thr Ala Ser Leu Gly
            20                  25                  30

Tyr Asp Tyr Ile Glu Ala Pro Ala Leu Asp Pro Ser Leu Ile Asp Ile
         35                  40                  45

Asp Phe Thr Arg Lys Ala Leu Glu Lys His Gly Leu Gly Ile Thr Thr
 50                  55                  60

Ser Leu Gly Leu Asp Asp Ser Cys Asp Ile Ser Ser Gly Asp Pro Asp
 65                  70                  75                  80

Lys Lys Ala Arg Gly Gln Ala His Leu Met Lys Val Val Ser Thr Thr
                 85                  90                  95

```
Arg Asp Leu Gly Gly Thr His Ile Thr Gly Ile Leu Tyr Ser Gly Phe
            100             105             110

Gln Lys Tyr Phe Thr Pro Ala Thr Pro Glu Gly Val Ala Gly Ala Val
        115             120             125

Glu Val Leu His His Val Ala Glu Glu Ala Ala Lys Ser Asn Ile Thr
    130             135             140

Leu Gly Leu Glu Val Val Asn Arg Tyr Glu Thr Asn Val Ile Asn Thr
145             150             155             160

Ala Ala Gln Gly Val Glu Leu Cys Lys Arg Val Gly Met Pro Asn Val
                165             170             175

Lys Val His Leu Asp Cys Tyr His Met Asn Ile Glu Glu Ala Asp Ala
            180             185             190

Glu Arg Ala Ile Ile Asp Thr Gly Asp Tyr Leu Gly Tyr Phe His Thr
        195             200             205

Gly Glu Ser His Arg Gly Tyr Leu Gly Thr Gly Ser Ile Asp Phe Thr
        210             215             220

Arg Ile Phe Arg Gly Leu Val Lys Ala Asn Tyr Gln Gly Pro Ile Cys
225             230             235             240

Phe Glu Ser Phe Ser Ser Ala Val Ala Gly Glu Pro Leu Ser Gly Ile
            245             250             255

Leu Gly Ile Trp Arg Asn Leu Trp Thr Asp Ser Thr Asp Leu Cys Arg
            260             265             270

His Ala Met Gln Phe Thr Gln Ala Gln Met Gln Ala Ala Glu Gln Ala
            275             280             285

Gln Ser Ile Arg Thr Gly Ala Asp Trp
        290             295
```

METHOD FOR PRODUCING D-PSICOSE FROM D-PSICOSE BORATE COMPLEX USING CHROMATOGRAPHY AND COMPOSITION CONTAINING D-PSICOSE

This application is a National Stage Application of International Application No. PCT/KR2018/007100, filed Jun. 22, 2018, which claims benefit of Serial No. 10-2017-0079637, filed Jun. 23, 2017 in the Republic of Korea and which applications are incorporated herein by reference. To the extent appropriate, a claim of priority is made to each of the above disclosed applications.

TECHNICAL FIELD

The present application relates to a method for producing D-psicose from a D-psicose borate complex using a chromatography and a composition containing D-psicose.

BACKGROUND ART

D-psicose is a natural sugar present in an extremely small amount in fruits such as figs and raisins and is a monosaccharide having a sweetness of 70% of that of sugar. It is well known that unlike fructose or sugar, D-psicose is not metabolized in human body and thus contains almost no calories, does not influence on hyperglycemia and is healthful for teeth with its non-cariogenic and anti-cariogenic properties.

Thus, there is a growing interest in D-psicose as a sweetener, but due to the rare existence of D-psicose in nature, there is a need to develop a technology that efficiently produces D-psicose for applying to the food industry.

Thus, as a method for producing D-psicose, the present inventors reported a method for economically producing D-psicose by isomerizing glucose to fructose and reacting the fructose with immobilized bacterial cells that produce D-psicose epimerization enzyme (Korean Patent Publication No. 10-2011-0035805, hereinafter, referred to as 'enzymatic conversion method'), and it has been know that using a borate in such an enzymatic conversion method remarkably increases a D-psicose conversion rate (Process Biochemistry 44 (2009) 22-828, *APPLIED AND ENVIRONMENTAL MICROBIOLOGY*, May 2008, p. 3008-3013).

However, in order to apply the enzymatic conversion method using the borate for industrial production, it is needed to develop a process considering economic feasibility that enables separating, collecting and recycling the borate used in the enzymatic conversion method. Additionally, since WHO (World Health Organization) suggests the content of boron included in drinking water to be 0.5 ppm or lower, there is a need for removing boron.

The borate used in the enzymatic conversion method is present in a boric acid ($H_3BO_3$) form in a sugar solution formed by the enzymatic conversion method, and is substantially not present in an ionic state because the pKa value of the borate is approximately 9 and most of the borate is present in a non-dissociated state in the enzymatic conversion reacting solution (having a pH of 5 to 7).

For conventional techniques for removing a borate, reported are a method in which a borate is converted into a poly-borate by supplying an alkaline agent to adjust the pH to be 9 to 11, and then a low-pressure reverse osmotic filtration is performed to remove the borate (Korean Patent No. 10-1384992), and a method in which the pH is adjusted to a range of 9.0 to 10.5 in order to eliminate scale which lowers a borate removal efficiency and then reverse osmotic process is performed to remove the borate (Korean Patent Application No. 10-1030192). However, the liquid psicose produced with an enzymatic conversion method has problems in that cost for bleaching is increased due to a rapid decline of color value when the pH is converted to alkaline range, a psicose content varies due to alkaline polymerization reaction, and an economic feasibility for industrialization becomes poor due to need for an additional process for removing the introduced alkaline agent.

Under such circumstances, as a result of earnestly conducting researches to efficiently separate and remove the borate remaining in the psicose produced with the enzymatic conversion method using a borate, the present inventors have accomplished the present application by confirming that simulated moving bed chromatography is used to be capable of effectively separating a psicose-containing fraction from a fraction containing a fructose and a borate.

DISCLOSURE OF THE APPLICATION

Technical Problem

An aspect of the present application provides a method for producing D-psicose, the method comprising: a step of putting a composition comprising a D-psicose borate complex into a chromatography comprising divalent cations; and a step of separating the composition comprising the D-psicose borate complex into a D-psicose containing fraction (i) and a borate-containing fraction (ii).

Another aspect of the present application provides a composition comprising D-psicose, wherein a content of the D-psicose is equal to or higher than 99% (w/w) and lower than 100% (w/w) on a dry solid basis, and a content of a borate is more than 0 and lower than 0.5 ppm (w/w).

TECHNICAL SOLUTION

Hereinafter, the present application will be described in detail.

Each of the descriptions and exemplary embodiments disclosed herein may be applied to other descriptions and exemplary embodiments. That is, all of the combinations of various factors disclosed herein belong to the scope of the present disclosure. Furthermore, the scope of the present application should not be limited by the specific descriptions provided hereinafter.

In order to achieve the objective of the present application, an aspect of the present application provides a method for producing D-psicose, the method comprising: a step of putting a composition comprising a D-psicose borate complex into a chromatography comprising divalent cations; and a step of separating the composition comprising the D-psicose borate complex into a D-psicose containing fraction (i) and a borate-containing fraction (ii).

Also, the method for producing the D-psicose in the present application may further comprise, before the step of putting, a step of obtaining a composition comprising the D-psicose borate complex by bringing a D-fructose and a borate into contact with a D-psicose 3-epimerization enzyme, a strain expressing the enzyme or a culture of the strain.

As used herein, the term "fractionation" generally refers to, a manipulation of separating each component or a specific group from various constituents, a mixture or a composition by means of a chromatography method and etc. Accordingly, a substance separated from specific components obtained by such manipulation is expressed as a "fraction" in the present application, to distinguish from fractionation.

Consequently, a D-psicose-containing fraction refers to a substance obtained by a chromatography separation manipulation from the compositions comprising a D-psicose borate complex. Additionally, a borate-containing fraction refers to a fraction excluding D-psicose-containing fraction, among the compositions comprising a D-psicose borate complex. Specifically, separation of psicose fraction and borate fraction in the present application may be classified as a separation after the fraction in which the amount of borate and/or fructose is maximal in fraction solid basis of borate and/or fructose, and before a fraction in which the amount of psicose is maximal in fraction solid basis of psicose in the fraction. Additionally, after a fraction in which the content of borate and/or fructose is maximal, fractions can be separated after the purity of borate and/or fructose is 80% (w/w) or lower, 15% (w/w) or lower, or 1% (w/w) or lower compared to the fraction in which the content of fructose is maximal, and before a fraction in which the content of a psicose is maximal, a classification can be made to a point before the purity of psicose is 70% (w/w) or lower, 10% (w/w) or lower, 1% (w/w) or lower or 0.4% (w/w) or lower compared to the fraction in which the content of psicose is maximal.

A D-psicose 3-epimerization enzyme (hereinafter, referred to as "psicose epimerization enzyme") of the present application may include, but not limited to, any protein that has an activity of epimerizing a D-fructose to a D-psicose, and a strain endogenously expressing the protein, a strain transformed to express the protein, a culture of the strain or a protein isolated from the culture may be used as the psicose epimerization enzyme.

The D-psicose 3-epimerization enzyme of the present application may be a wild-type psicose epimerization enzyme derived from *Agrobacterium tumefaciens* or *Kaistia granuli* or a variant thereof, and specifically, a psicose epimerization enzyme that has a genetic homology of at least 70%, at least 80%, at least 90%, at least 95%, at least 97%, at least 99% or 100% to the amino acid sequence of SEQ ID NO: 1, 2, 3 or 4. Additionally, it should be interpreted that as long as an amino acid sequence with such a homology has a psicose epimerization enzyme activity, the amino acid sequences certain of which are partially deleted, modified, substituted or added should be included in the scope of the amino acid sequence of the present application. More specifically, the psicose epimerization enzyme may have the amino acid sequence of SEQ ID NO: 1 or 4.

The strain of the present application may be, but not limited to, *Corynebacterium glutamicum* KCCM11403P (Korean Patent No. 10-1455795).

The D-fructose of the present application may be produced by hydrolysis of sucrose or isomerizing glucose. By such, mass-production of psicose is possible by producing D-psicose at a high yield using generalized and inexpensive raw materials, such as fructose, sucrose and glucose. Additionally, a borate is a salt in which a hydrogen atom of a boric acid is substituted to a metal element, and a commercially available product may be used as is.

Additionally, the method of the present application for producing D-psicose may additionally comprise a step of removing metal ions by flowing a sugar solution through a pharmaceutical regeneration type ion exchange device (for example, a two-bed, three-tower type ion exchange device or a two-bed, two-tower type ion exchange device). The step of removing the metal ions may be additionally included after the step of acquiring a composition comprising the D-psicose borate complex and/or before the step of putting a composition comprising the D-psicose borate complex into a chromatography comprising divalent cations.

According to the present application, the composition of the present application comprising the D-psicose borate complex may have the borate content of less than 25% (w/w) on a dry solid basis. Specifically, the composition of the present application may have the borate content of 6.25%-25% (w/w) or 6.25%-21.05% (w/w) on a dry solid basis.

According to the present application, the fraction of the present application comprising the D-psicose may have the borate content of less than 0.5 ppm (w/w) on a dry solid basis. Specifically, the fraction comprising the D-psicose may have, on a dry solid basis, the borate content of 0.1-0.45 ppm (w/w), 0.05-0.45 ppm (w/w), 0.1-0.4 ppm (w/w), 0.05-0.39 ppm (w/w), 0.1-0.39 ppm (w/w), or 0.05-0.35 ppm (w/w).

According to the present application, the fraction of the present application comprising the D-psicose may have the D-psicose content of 85% (w/w) or more on a dry solid basis. Specifically, the fraction of the present application comprising the D-psicose may have, on a dry solid basis, the D-psicose content of 85%-99.9% (w/w), 90%-99.9% (w/w), 90%-99.5% (w/w), 91%-99.9% (w/w), 91%-99.5% (w/w), 98.0%-99.9% (w/w), 98.0%-99.5% (w/w), 99.0%-99.9% (w/w), or 99.0%-99.5% (w/w).

Additionally according to the present application, the fraction of the present application comprising the D-psicose may comprise D-fructose, and specifically, may have, on a dry solid basis, the D-fructose content of 10% (w/w) or less, more specifically 0.1%-9.9% (w/w), 0.1%-9.5% (w/w), 0.2%-9.5% (w/w), 0.1%-9% (w/w), 0.1%-5% (w/w), 0.1%-2% (w/w), or 0.1%-1% (w/w).

According to the present application, the chromatography is a simulated moving bed (SMB) chromatography and may comprise a columnar form filled with a cation exchange resin. Such divalent cation may be a calcium ion ($Ca^{2+}$), a barium ion ($Ba^{2+}$), a strontium ion ($Sr^{2+}$), etc., and specifically may be a calcium ion.

Additionally, according to the present application, the simulated moving bed chromatography may comprise 4 or more columns. Additionally, the simulated moving bed chromatography of the present application may perform elution with water of 50-70° C. Specifically, the elution may be performed with water of 55-65° C. or 58-62° C.

Furthermore, according to the present application, the composition comprising the D-psicose borate complex may have a pH of 5-7, and the pH of the composition may be adjusted or maintained to be 5-7 prior to the step of putting the composition comprising the D-psicose borate complex into a chromatography comprising divalent cations. By having the pH of the composition comprising the D-psicose borate complex to be 5-7, phenomena such as coloration by D-psicose degradation may be prevented.

Additionally, according to the present application, a step of removing a small amount of the remaining borate by flowing the D-psicose-containing fraction (i) through an ion exchange tower filled with a boron-selective ion exchange resin may be additionally included.

Any substance that may selectively adsorb boron may be used as the cation exchange resin (adsorbent) filled in the column of the present application, and specifically, Amberlite IRA743 and Purolite S108 may be examples in which a polyhydric alcohol group is introduced as a functional group.

Additionally, according to the present application, the borate-containing fraction (ii) may be 95 or higher parts by weight with respect to 100 parts by weight of the borate content in the composition comprising the D-psicose borate complex.

Additionally, according to the present application, the composition comprising the D-psicose borate complex may further comprise a fructose. In this case, the borate content in the borate-containing fraction (ii) may be 95 or higher parts by weight with respect to 100 parts by weight of the borate content in the composition comprising the D-psicose borate complex, and the fructose content may be 95 or higher parts by weight with respect to 100 parts by weight of the fructose content in the composition comprising the D-psicose borate complex.

The borate content and the fructose content in the borate-containing fraction (ii) may be a sum of the D-psicose-containing fraction (i) and the borate-containing fraction (ii) rather than the parts by weight of the composition comprising the D-psicose borate complex, and specifically, the borate content and the fructose content may be 95 or more, 96 or more, 97 or more, 98 or more, 99 or more, 99.1 or more, or 99.5 or more parts by weight, and may not exceed 100 parts by weight.

The borate in the borate-containing fraction (ii) may be reused by comprising, within aforementioned ranges, the borate and the fructose in the borate-containing fraction (ii).

In another aspect of the present application, the present application provides a composition comprising D-psicose in which the content of D-psicose is 85%-99.9% (w/w) on a dry solid basis, and the content of borate is more than 0 and less than 0.5 ppm (w/w).

The composition comprising the D-psicose comprises 10% (w/w) or less of D-fructose on a dry solid basis. Additionally, the composition comprising the D-psicose is a fraction comprising the D-psicose separated with a chromatography.

A detailed description related to the aspect will be omitted herein because the description related to the aforementioned method for producing D-psicose is similarly applicable to this aspect.

The present invention will now be simply explained with reference to FIG. 4 that illustrates a D-psicose production flowchart. First, as a step (1), fructose and borate are mixed, and as a step (2), a D-psicose 3-epimerization enzyme is then brought into contact with the mixture obtained from the step (1) to perform an enzymatic reaction process. Next, as a step (3), D-psicose, residual fructose and a D-psicose borate complex which is a borate are obtained, and thereafter, as a step (4), a D-psicose fraction (i) and a borate fraction (ii) are separated using an SMB chromatography. The borate fraction (ii) obtained from the step (4) comprises the residual fructose and borate, and may thus be reused by returning to the step (1). Furthermore, as mentioned above, the D-psicose fraction (i) obtained from the step (4) may be made to flow through an ion exchange tower filled with a boron-selective ion exchange resin to remove additionally a small amount of a remaining borate, if necessary.

Advantageous Effects

A method for separating a borate and a method for producing psicose in the present application exhibit the effect in which a borate remaining in psicose, which is produced by an enzymatic conversion method using a borate, can be efficiently separated and removed.

Additionally, when the method of the present application is used for producing psicose, fructose and borate, which are raw materials, can be effectively separated from psicose, and thus enabling raw materials to be recycled.

MODE FOR CARRYING OUT THE INVENTION

Hereinafter, the present invention will be described in more detail with reference to the accompanying examples. However, the examples are to explain the present application by way of example only, and thus the scope of the present application is not limited by the examples. Details not included herein are readily recognized and appreciated to those skilled in the art at the time of filing the present application, and the description therefore will thus be omitted.

Example 1: Production of D-Psicose Using Borate and Enzymatic Conversion Method

An enzymatic conversion reaction was carried out using *Corynebacterium glutamicum* (KCCM11403P), which is a recombinant strain known to express a variant of a psicose epimerase derived from *Agrobacterium tumefaciens* (Korean Patent No. 10-1455759). 0.1 M fructose was dissolved in water and 0.05 M borate and 10 mM $MnCl_2$ were added thereto (experimental example 1) or only 10 mM $MnCl_2$ was added thereto (comparative example 1) to prepare a raw material for enzymatic conversion reaction. Then, the strain (20% w/w) was added to the raw material and the reaction was carried out for 3 hours under the condition of pH of 8.0 and the temperature of 55° C.

Afterwards, the conversion rate was calculated by comparing the peak area values of the substrate (D-fructose) of the psicose epimerization enzyme and the product (psicose) through HPLC analysis, and the HPLC analysis was performed under the conditions that the sample is injected to a column (BP-100 $Ca^{2+}$ carbohydrate column) set at 80° C. and distilled water as a mobile phase flows at a rate of 0.6 ml/min through the column.

Figure 1:
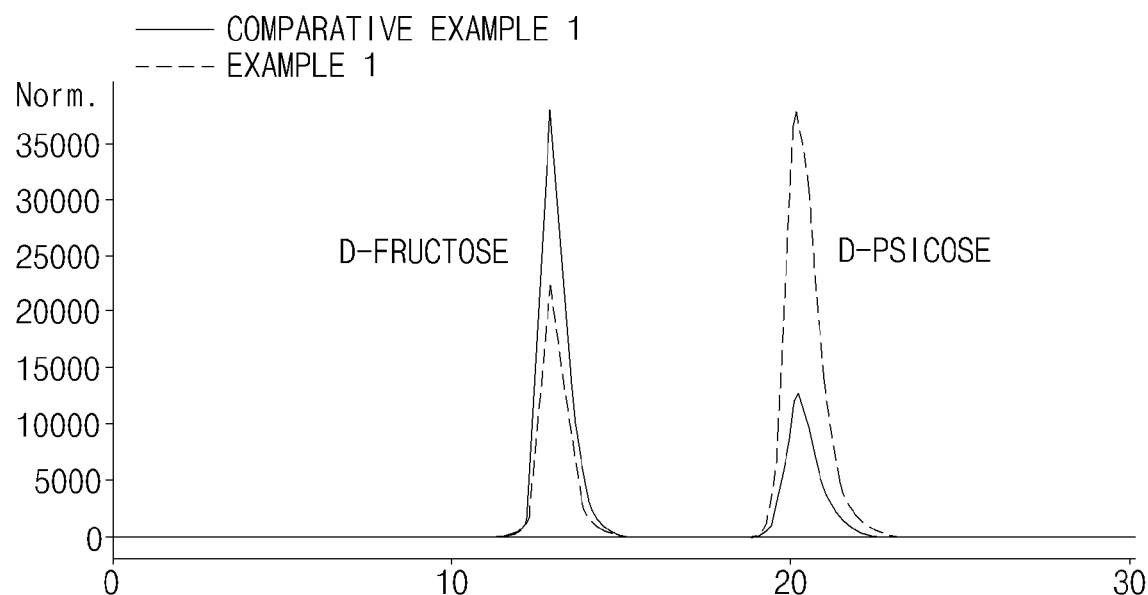
FIG. 1 is a HPLC chromatogram for the results of converting D-fructose to D-psicose, respectively obtained when a borate is added (experimental example 1) and not added (comparative example 1) to a D-psicose epimerization enzyme reaction of example 1 of the present application.
Figure 2:
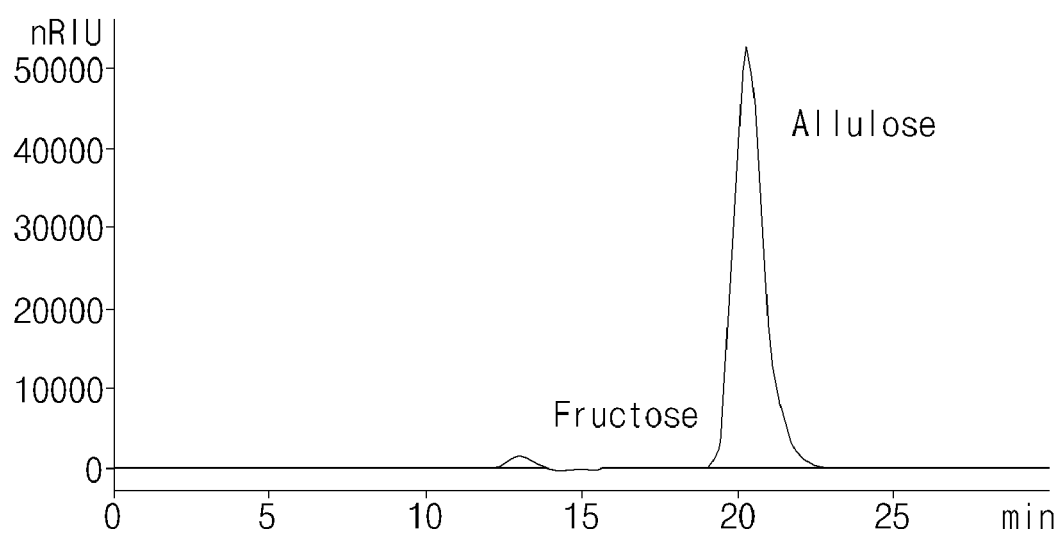
FIG. 2 is a HPLC chromatogram of a D-psicose fraction fractionated by the simulated moving bed (SMB) chromatography of the present application.

As a result, the conversion rate to D-psicose was 25% for comparative example 1, but 56% for experimental example 1. Thus, it could be confirmed that the conversion rate of experimental example 1 was increased by 224% compared to that of comparative example 1 (FIG. 1).

Example 2: Borate Separation 2-1. Confirmation of Borate Separation Using SMB Chromatography An SMB (Simulated Moving Bed) chromatography was used to separate borate-removed D-psicose from a composition comprising D-psicose borate complex (borate, D-fructose and D-psicose, hereinafter referred to as "feed"). The SMB chromatography used an advanced simulated moving-bed system (Organo, Japan) instrument, and the instrument includes successively connected six columns (each having a height of 1.2 m, and a diameter of 4.3 cm), a feed pump, a recirculation pump, an eluent pump, a heat exchanger and a valve for controlling flow rate. The conditions for operating the SMB chromatography are as the Table 1 below.

TABLE 1

| Feed | Mixture of fructose, psicose and borate |
|---|---|
| Feed concentration | 60% (w/w) |
| Cation exchange resin (adsorbent) filled in columns | Amberlite (Amberlite CR-1310; Ca-type) |
| Size and number of columns | 43 mm × 1200 mm * 6 columns |
| Desorbent (eluent) | O |
| Flow speed | 2.49 m/H |
| Eluent temperature | 60° C. |

Figure 3:
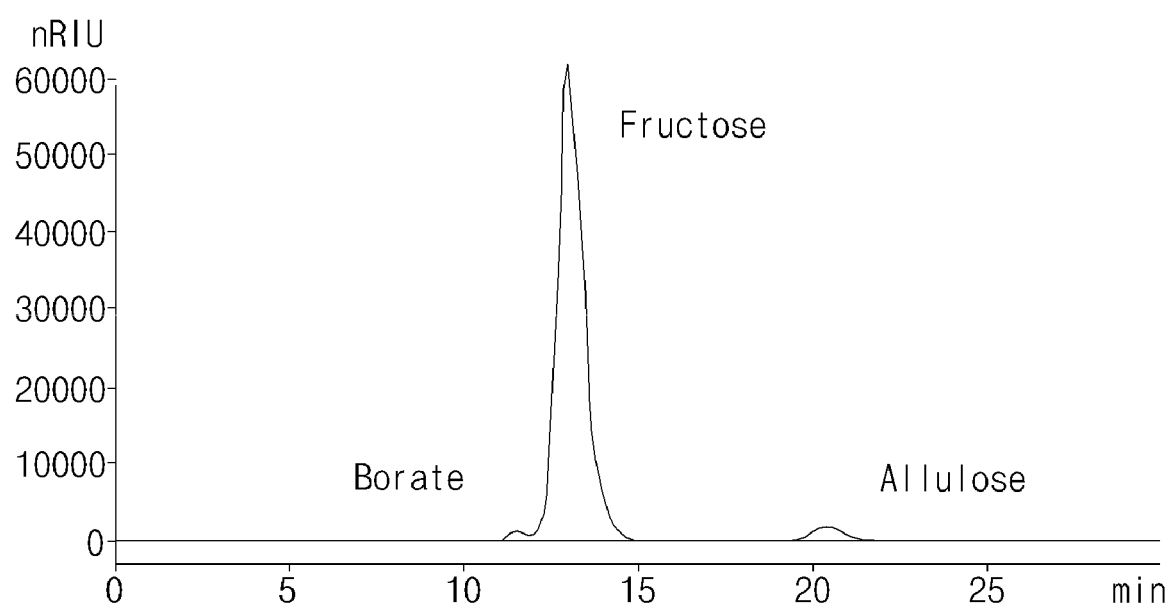
FIG. 3 is a HPLC chromatogram of a borate fraction fractionated by the simulated moving bed (SMB) chromatography of the present application.
Figure 4:
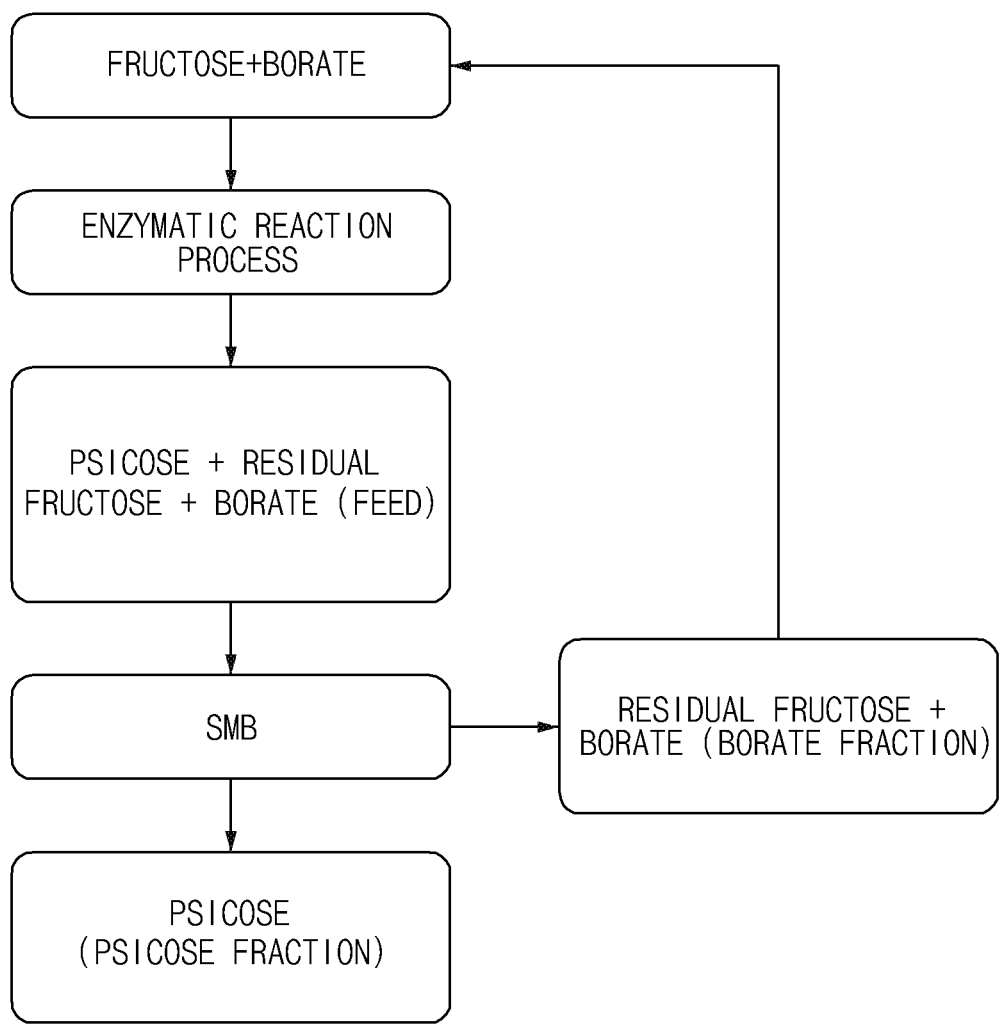
FIG. 4 is a D-psicose production flowchart of the present application.

Additionally barium ions ($Ba^{2+}$) and strontium ions ($Sr^{2+}$), as divalent cations, were filled and used instead of calcium ions, and an experiment using sodium ions ($Na^+$), as monovalent cations, was additionally performed as a control group. As a result, it was confirmed that the amounts of the borate remaining in a psicose fraction in the case of using calcium ions, strontium ions and barium ions were 0.2 ppm, 0.3 ppm and 0.4 ppm respectively, which are lower than the boron content standard in drinking water recommended by WHO, which is 0.5 ppm, and the rate of removal was 99.999% (DS %, w/w). On the other hand, it was confirmed that the psicose fraction in the case of using sodium ions was 62100 ppm, which is a significantly higher value than 0.5 ppm. Additionally, the purities of a psicose in psicose fractions were 99.350% (DS %, w/w) (FIG. 3), 99.150% (DS %, w/w) and 90.850% (DS %, w/w), respectively. Additionally compared to those of the feed, the recovery rate of the borate were found to be approximately 100% for the borate fraction in the case of using calcium ions and strontium ions and the recovery rate of the fructose was 99.264%, which was a high recovery rate (borate content in borate fraction/(psicose fraction+borate fraction)*100). Thus a fructose and a borate, which are the raw materials used for producing a psicose, can be separated while obtaining a high-purity psicose using the SMB chromatography (see Table 2 and FIG. 3), and therefore it could be confirmed that the fructose and the borate remaining after production of the psicose could be reused (FIG. 4).

TABLE 2

| | Feed | Psicose fraction | Borate fraction |
|---|---|---|---|
| Amberlite (Amberlite CR-1310; Ca-type) | | | |
| Borate (DS %, w/w) | 12.050 | 0.00002 | 12.050 |
| D-psicose (DS %, w/w) | 49.255 | 99.350 | 0.280 |
| D-fructose (DS %, w/w) | 38.695 | 0.650 | 87.670 |
| Amberlite (Amberlite CR-1310; Sr-type) | | | |
| Borate (DS %, w/w) | 12.050 | 0.00003 | 12.050 |
| D-psicose (DS %, w/w) | 49.255 | 99.150 | 0.350 |
| D-fructose (DS %, w/w) | 38.695 | 0.850 | 87.600 |
| Amberlite (Amberlite CR-1310; Ba-type) | | | |
| Borate (DS %, w/w) | 12.050 | 0.00004 | 12.050 |
| D-psicose (DS %, w/w) | 49.255 | 90.850 | 8.750 |
| D-fructose (DS %, w/w) | 38.695 | 9.150 | 79.200 |
| Amberlite (Amberlite CR-1310; Na-type) | | | |
| Borate (DS %, w/w) | 12.050 | 6.210 | 8.870 |
| D-psicose (DS %, w/w) | 49.255 | 55.850 | 37.280 |
| D-fructose (DS %, w/w) | 38.695 | 37.940 | 53.850 |

*DS: Dry solid 2-2. Confirmation of Content of Borate Separable by SMB Chromatography The purity of psicose in a psicose fraction was 99% (DS %, w/w) or higher and 0.5 ppm or less of boron concentration in drinking water recommended by WHO was satisfied, whereby it could be confirmed that SMB chromatography is applicable for such a borate content in feed. The contents of borate, psicose and D-fructose in the feed are as the Table 3 below.

As a result, it could be confirmed that when the quantity of added borate was 21.05% (DS %, w/w) or less, the rate of borate removal was all 99.999%, the quantity of borate remaining in the psicose fraction was 0.5 ppm (w/w) or less, and the purity of psicose was 99% (DS %, w/w) or more (Table 3).

TABLE 3

| | | Experimental example 2 | Experimental example 3 | Experimental example 4 | Experimental example 5 | Experimental example 6 | Experimental example 7 |
|---|---|---|---|---|---|---|---|
| Borate content in feed (DS %, w/w) | | 0.00 | 6.25 | 11.76 | 16.67 | 21.05 | 25.00 |
| Content of Borate psicose fraction (DS %, w/w) | | 0 | 0.000015 | 0.000021 | 0.000032 | 0.000044 | 0.000137 |
| | D-fructose | 0.78 | 0.75 | 0.68 | 0.56 | 0.54 | 1.23 |
| | Psicose | 99.22 | 99.25 | 99.32 | 99.44 | 99.46 | 98.77 |

*DS: Dry solid

The present application has been described above in detail with reference to the specific features, and it will be apparent to those skilled in the art that this detailed description is only for a preferred embodiment and does not limit the scope of the present application. Thus, the substantial scope of the present invention will be defined by the appended claims and equivalents thereof.

The invention claimed is:

1. A method for producing D-psicose, the method comprising:
   a step of putting a composition comprising a D-psicose borate complex into a chromatography comprising divalent cations; and
   a step of separating the composition comprising the D-psicose borate complex into a D-psicose-containing fraction (i) and a borate-containing fraction (ii); and
   wherein the chromatography is a simulated moving bed chromatography.

2. The method of claim 1, further comprising, before the step of putting, a step of obtaining a composition comprising the D-psicose borate complex by bringing a D-fructose and a borate into contact with a D-psicose 3-epimerization enzyme, a strain expressing the enzyme or a culture of the strain.

3. The method of claim 2, wherein the D-psicose 3-epimerization enzyme is a wild-type psicose epimerization enzyme derived from *Agrobacterium tumefaciens* or *Kaistia granuli*, or a variant thereof.

4. The method of claim 1, wherein the composition comprising the D-psicose borate complex has a borate content of less than 25% (w/w) on a dry solid basis.

5. The method of claim 1, wherein the D-psicose-containing fraction (i) has a borate content of less than 0.5 ppm (w/w) on a dry solid basis.

6. The method of claim 1, wherein the D-psicose-containing fraction (i) has a D-psicose content of 85% (w/w) or more on a dry solid basis.

7. The method of claim 1, wherein the divalent cations are included in a columnar form filled with a cation exchange resin.

8. The method of claim 1, wherein the divalent cations are one or more of calcium ions, barium ions, and strontium ions.

9. The method of claim 7, wherein the simulated moving bed chromatography comprises four or more columns.

10. The method of claim 7, wherein the simulated moving bed chromatography performs elution with water of 50-70° C.

11. The method of claim 1, wherein a content of the borate-containing fraction (ii) is 95 or higher parts by weight with respect to 100 parts by weight of a borate content in the composition comprising the D-psicose borate complex.

12. The method of claim 1, wherein the composition comprising the D-psicose borate complex further comprises a fructose.

13. The method of claim 12, wherein the borate-containing fraction (ii) has a borate content of 95 or higher parts by weight with respect to 100 parts by weight of a borate content in the composition comprising the D-psicose borate complex, and has a fructose content of 95 or higher parts by weight with respect to 100 parts by weight of a fructose content in the composition comprising the D-psicose borate complex.

* * * * *